United States Patent [19]
Mena

[11] Patent Number: 5,533,898
[45] Date of Patent: *Jul. 9, 1996

[54] DENTAL IMPLANT DEVICE

[76] Inventor: Raul Mena, 201 N. University Dr. Suite 101, Plantation, Fla. 33324

[*] Notice: The term of this patent shall not extend beyond the expiration date of Pat. No. 5,376,004.

[21] Appl. No.: 333,808

[22] Filed: Nov. 3, 1994

Related U.S. Application Data

[63] Continuation of Ser. No. 154,367, Nov. 18, 1993, Pat. No. 5,376,004.

[51] Int. Cl.$^6$ .................................................. A61C 8/00
[52] U.S. Cl. ........................................ 433/173; 433/174
[58] Field of Search .................................. 433/172, 173, 433/174, 175, 176, 221, 225

[56] References Cited

U.S. PATENT DOCUMENTS

| | | | |
|---|---|---|---|
| 4,466,796 | 8/1984 | Sandhaus | 433/173 |
| 4,738,623 | 4/1988 | Driskell | 433/173 |
| 4,850,870 | 7/1989 | Lazzara et al. | 433/173 X |
| 4,854,872 | 8/1989 | Detsch | 433/173 |
| 4,906,191 | 3/1990 | Soderberg | 433/173 X |
| 4,976,739 | 12/1990 | Duthie | 433/174 |
| 5,030,095 | 7/1991 | Niznick | 433/174 X |
| 5,259,759 | 11/1993 | Jorneus et al. | 433/173 |
| 5,269,686 | 12/1993 | James | 433/173 |

Primary Examiner—Nicholas D. Lucchesi
Attorney, Agent, or Firm—J. Sanchelima

[57] ABSTRACT

A dental implant device for mounting prosthesis and minimizing the lodging of extraneous substances in interstitial spaces. A root form implant fixture is permanently implanted in a user's jaw bone. The fixture includes anchorage and engagement sections. The engagement section includes a cylindrical portion adjacent to the anchorage section, a beveled portion that is adjacent to and coaxially disposed with respect to the cylindrical portion and a hexagonal portion adjacent to and coaxially disposed with respect to the beveled portion.

6 Claims, 3 Drawing Sheets

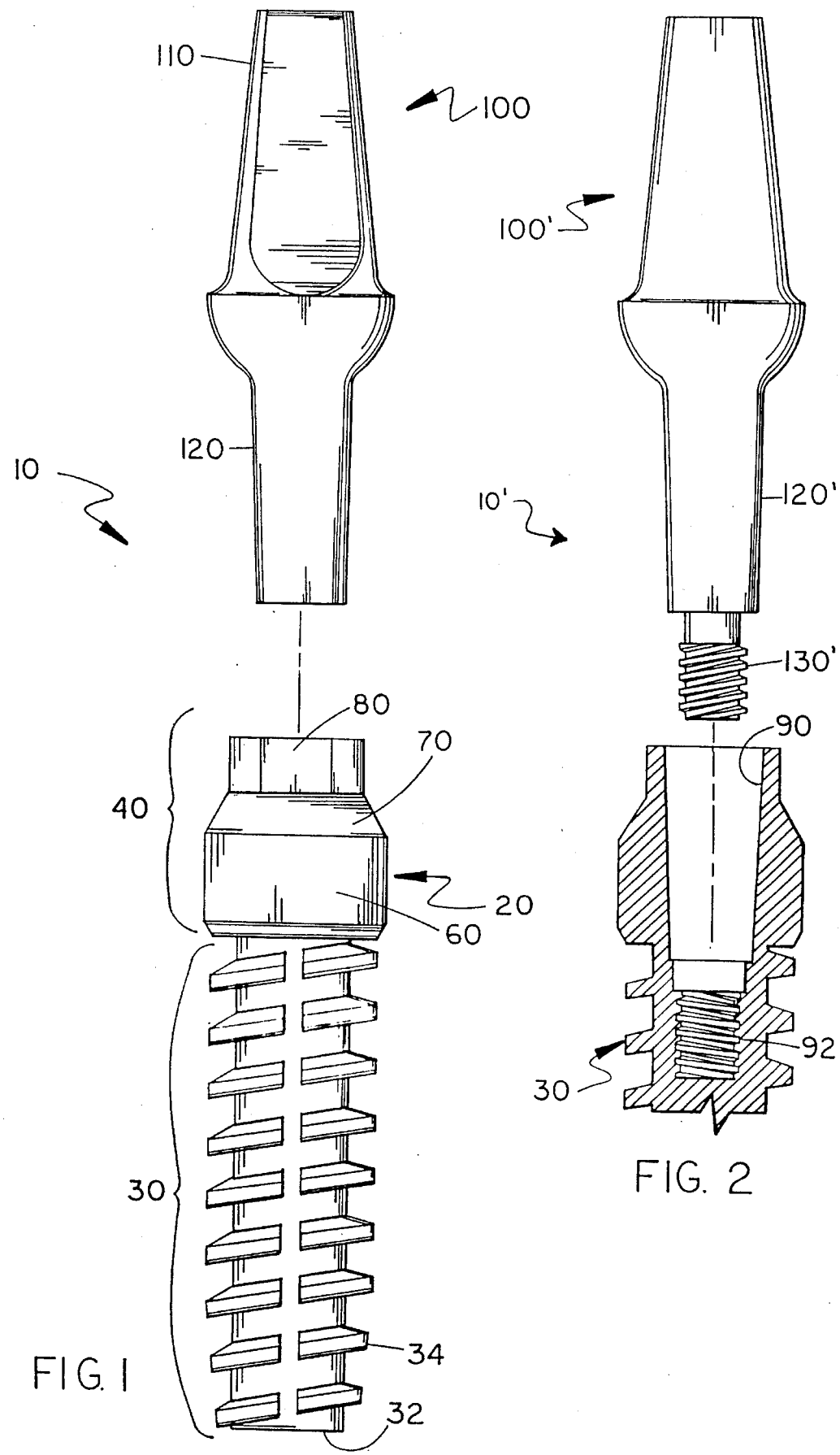

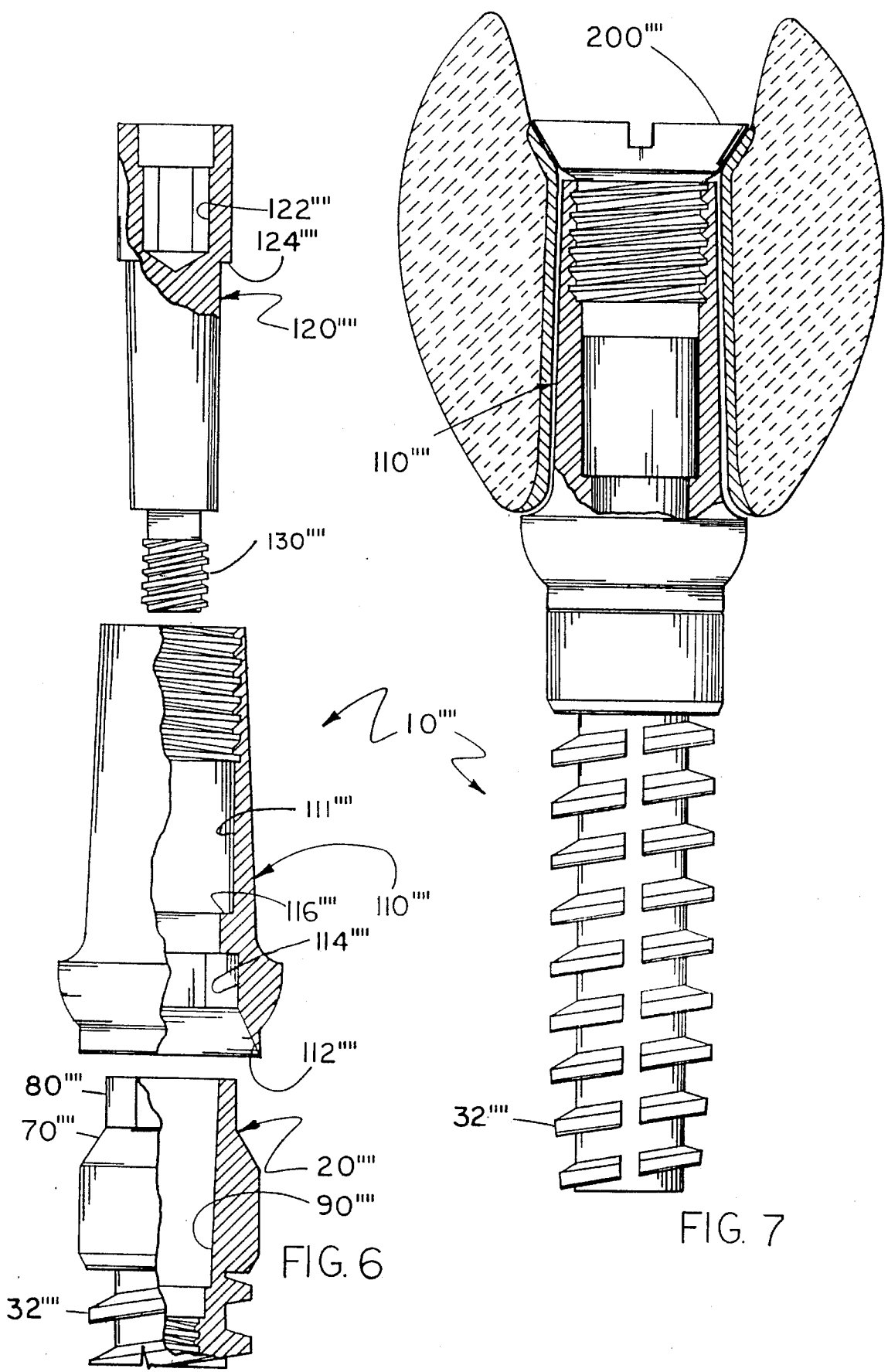

DENTAL IMPLANT DEVICE

The present application is in continuation of application Ser. No. 08/154,367, allowed and filed on Nov. 18, 1993, now U.S. Pat. No. 5,376,004.

BACKGROUND OF THE INVENTION

1. Field of the Invention

The present invention relates to dental implants.

2. Description of the Related Art

Applicant believes that the closest reference corresponds to the implants sold by Stryker Dental Implants, Kalamazoo, Mich. 49001 and particularly, Stryker Fin Implant model nos. 260-135-008 and equivalents. However, this differ from the present invention because they fail to provide a termination having a multi-sided body (hexagonal portion) and a beveled portion adjacent thereto with the consequent compatible interface surface for engaging a prosthetic abutment free from debris traps. Also, the prior art fails to teach an anti-rotational mechanism for the abutment further, the prior art does not disclose a cylinder root form implant fixture with helical grooves or a screw type root form.

Another relevant reference is Duthie, Jr.'s patent wherein a dental implant that includes implant means 12 is disclosed with an abutment 44 that includes a frustoconical post member 40. Member 40 includes a distal and narrowest end 40 *b* that mates with tapered cavity 32 *b*. However, Duthie, Jr. fails to disclose a multi-face portion adjacent to an coaxially disposed with respect to the inwardly beveled portion. Also, Duthie, Jr. does not disclose an inwardly extending beveled portion. Duthie, Jr. also lacks a cylindrical portion since thread block section 26 is really part of the shaft. In fact, the purpose of the thread block section 26 is to permit bone to grow there. See column 4, line 18. This is not the purpose of cylindrical portion 60.

SUMMARY OF THE INVENTION

It is one of the primary objects of the present invention to provide an implant device that is free from debris traps or pockets where saliva, blood bacteria, soft tissue invagination or any other substances can be collected.

It is another object of the present invention to provide an implant device that includes a beveled portion for cooperative engagement with a cooperating abutment.

Still another object of the invention is to provide a versatile implant device to which different types of prosthetic abutments could be mounted.

Yet another object of this invention is to provide a hexagonal element that facilitates the application of the rotational force necessary to insert the implant in the bone and to prevent rotation of the abutment head on an individual or single tooth implant.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 represents a side elevational view of one of the preferred embodiments for a dental root form implant fixture of the threaded shaft type with an abutment having a smooth engagement tapered shaft.

FIG. 2 represents an alternate embodiment wherein the smooth engagement tapered shaft includes a threaded end, and the anchorage section is partially shown in cross-section taken along line 2 in FIG. 5.

FIG. 6 shows an elevational view of a fourth alternate embodiment, with partial cross-sections, having a removable abutment head.

FIG. 7 represents the components shown in FIG. 6 after being assembled.

DETAILED DESCRIPTION OF THE PREFERRED EMBODIMENT

Referring now to FIG. 1, where the preferred embodiment for the present invention is generally referred to with numeral 10, it can be observed that it basically includes root form implant fixture 20 and abutment member 100. Root form implant fixture 20 includes anchorage section 30 and engagement section (neck) 40.

Figure 3:
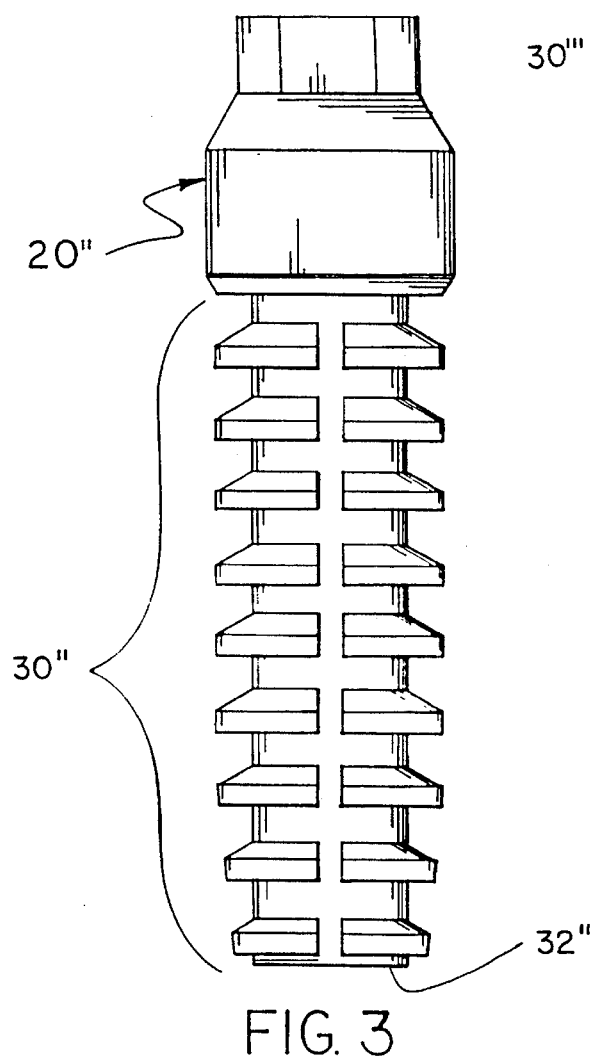
FIG. 3 represents a side elevational view of a second alternate embodiment for a root form implant fixture of the fin type.

Anchorage section 30 includes shaft 32 with threads 34 having sufficient separation of its threads to permit the bone in which it is inserted to occupy the space in between for best anchorage results. Shaft 32 can also be of the type known in the art as the fin type, as shown in FIG. 3, wherein several disks are rigidly positioned in a spaced apart parallel relationship with respect to each other, mounted to shaft 32. Another type of shaft 32 is the one shown in FIG. 4 and it corresponds to a cylinder with a helical groove.

As shown in FIG. 1, engagement section 40 is integrally built at one of the ends of shaft 32 and it includes cylindrical portion 60, beveled portion 70 and multi-face portion 80, all adjacent to each other in that order. Multi-face portion 80 has a hexagonal shape, in the preferred embodiment.

Central and longitudinally extending cavity 90 extends through the center of cylindrical, beveled and multi-face portions 70 and 80, as well as part of shaft 32, as best seen in FIG. 2. In the preferred as well as the alternate embodiment shown in FIG. 2, cavity 90 narrows down (tapers) as it extends toward anchorage section 30. At the end of cavity 90, in the alternate embodiment shown in FIG. 2, there is a threaded bottom part 92. It should be noted that for both, the preferred embodiment shown in FIG. 1 and the alternate embodiment of FIG. 2, the same cavity 90 is used even if the abutment's post 120 of the preferred embodiment lacks a mating thread.

Abutment member 100 has head 110 with elongated post 120 that is built in, as seen in FIG. 1. The angle of head 110 with respect to the longitudinal axis of member 100 varies depending on the correction for parallelism that may be necessary. In the figures applicant has shown abutments with 0 degrees of correction to facilitate the description of the invention. Lack of parallelism is undesirable and it arises when fixtures 20 are not positioned parallel to each other. Elongated post 120, in the preferred embodiment shown in FIG. 1, is smooth and bites against internal walls of central cavity 90 thereby locking it in place. The metal to metal biting engagement of post 120 and internal walls of cavity 90 provides a retention of abutment 100 and hermetic seal for any unoccupied space inside cavity 90 thereby preventing the collection of saliva, blood or any other decaying substance.

In FIG. 2, alternate abutment member 100' includes threaded pin 130' rigidly mounted at the distal end of post 120'. Threaded pin 130' cooperatively engages with threaded bottom part 92 of cavity 90.

Figure 5:
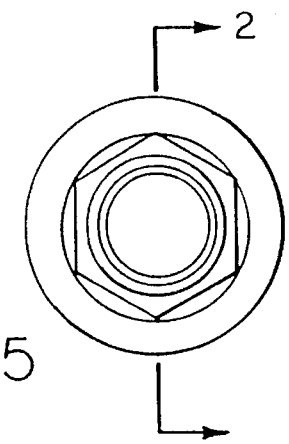
FIG. 5 is a top view of the second alternate embodiment.
Figure 4:
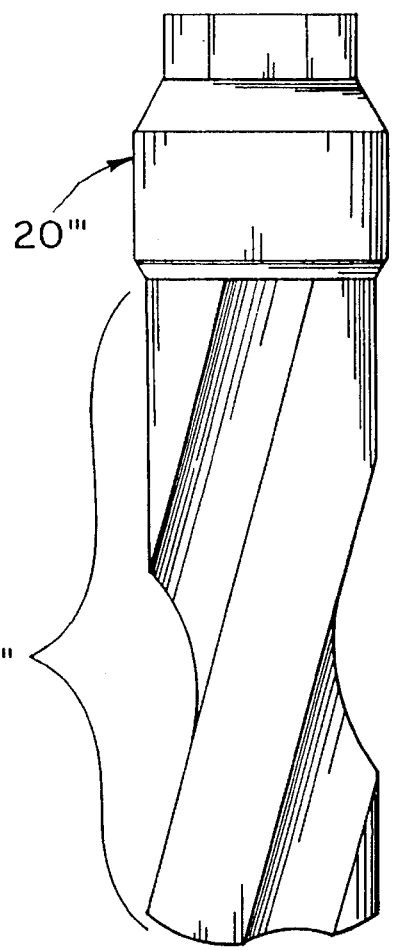
FIG. 4 is a partial representation of a third alternate embodiment for a cylinder form implant fixture of the helical groove type.

The second and third alternate embodiments shown in FIGS. 3 and 4 for fixtures 20" and 20''' are basically similar to those shown in FIGS. 1 and 2 except that shafts 32" and 32''' of anchorage sections 30" and 30''' are of the fin and helical groove types, respectively.

A fourth alternate embodiment is shown in FIG. 6 and is generally referred to with numeral 10''''. Root form implant fixture 20'''' used with dental implant device 10'''' is identical to the one used with devices 10 and 10'. Fixture 20'''' can be of any type (threaded, fin or cylinder). Abutment head 110'''' is removably mounted over fixture 20'''' and in cooperative non-rotational engagement thereon. Inwardly chamfered rim 112'''' matingly comes in complementary abutting contact with beveled portion 70''''. This flat face to face engagement of rim 112'''' and beveled portion 70'''' will create a hermetic seal that will prevent the infiltration of saliva, bacteria, exudate or soft tissue invagination or any other foreign bodies. Internal multi-faced socket 114'''' similarly matingly and cooperatively engages with multi-face portion 80'''', thereby preventing rotation of abutment 110".

Post 120'''' is coaxially inserted through central opening 111'''' of abutment head 110'''' and pin member 130'''' at one end protrudes through rim 112'''' to engage with cavity 90'''' in fixture 20''''. This engagement is accomplished in the same manner as described for the preferred and the first alternate embodiments. The only difference being that post 120'''' is also provided with an internal socket 122'''' to permit rotating it and causing sleeve 124'''' to come in contact with counterbore surface 116'''', thereby holding abutment head 110'''' down.

Screw member 200'''' is designed to hold the prosthesis (fixed or removable) to abutment head 110'''', as best seen in FIG. 7.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A dental implant device, comprising:
   A. form implant means adapted to be permanently implanted in a user's jaw bone having an anchorage section and an engagement section and said anchorage section includes a shaft having means for engaging to said bone, and said engagement section being integrally built on said anchorage section and further including a cylindrical portion adjacent to said anchorage section, said cylindrical portion having a diameter that is larger than the diameter of said shaft and coaxially disposed with respect thereto, an inwardly beveled portion that includes first and second ends, said first end having the same diameter as said cylindrical portion and being adjacent to and coaxially disposed with respect to said cylindrical portion and a multi-face portion coaxially adjacent to and connected to said second end of said beveled portion; and
   B. abutment means removably mounted to said form implant means.

2. The dental implant device set forth in claim 1 wherein said form implant means includes a centrally disposed tapered cavity and said abutment means includes a cooperating mating frustoconical post member having a distal end.

3. The dental implant device set forth in claim 2 wherein said post member includes a threaded pin member coaxially and rigidly mounted to the distal and narrowest end of said post member and said cavity including a threaded bottom portion for cooperatively receiving said pin member.

4. The dental implant device set forth in claim 3 wherein said form implant means is threaded.

5. The dental implant device set forth in claim 3 wherein said form implant means includes a plurality of fin members mounted thereto.

6. The dental implant device set forth in claim 3 wherein said form implant means includes a helical groove.

\* \* \* \* \*